(12) United States Patent
Sommer

(10) Patent No.: US 7,257,191 B2
(45) Date of Patent: Aug. 14, 2007

(54) MEDICAL EXAMINATION AND TREATMENT SYSTEM

(75) Inventor: Andres Sommer, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/287,101

(22) Filed: Nov. 23, 2005

(65) Prior Publication Data

US 2006/0113497 A1 Jun. 1, 2006

(30) Foreign Application Priority Data

Nov. 30, 2004 (DE) ............. 10 2004 057 726

(51) Int. Cl.
*A61N 5/10* (2006.01)
*G21G 4/08* (2006.01)
(52) U.S. Cl. ............ 378/65; 378/64; 250/492.3; 600/427; 600/436
(58) Field of Classification Search ............ 378/64, 378/65, 95, 97, 205, 207–209; 600/417, 600/427, 436; 250/492.3
See application file for complete search history.

(56) References Cited

U.S. PATENT DOCUMENTS

| 4,726,046 A * | 2/1988 | Nunan ................ 378/65 |
| 5,039,867 A * | 8/1991 | Nishihara et al. ......... 250/492.3 |
| 5,442,675 A * | 8/1995 | Swerdloff et al. ............ 378/65 |
| 6,385,286 B1 * | 5/2002 | Fitchard et al. ............... 378/65 |
| 6,509,573 B1 | 1/2003 | Badura et al. |
| 2003/0048868 A1 * | 3/2003 | Bailey et al. ................ 378/65 |
| 2004/0005027 A1 * | 1/2004 | Nafstadius ................ 378/65 |
| 2004/0096033 A1 * | 5/2004 | Seppi et al. ................ 378/65 |
| 2005/0017185 A1 * | 1/2005 | King ................ 250/370.05 |

FOREIGN PATENT DOCUMENTS

| DE | 35 02 776 | 1/1985 |
| DE | 38 28 639 | 8/1988 |
| DE | 198 35 209 | 8/1998 |

* cited by examiner

*Primary Examiner*—Edward J. Glick
*Assistant Examiner*—Anastasia S. Midkiff
(74) *Attorney, Agent, or Firm*—Brinks, Hofer, Gilson & Lione

(57) ABSTRACT

A medical examination and treatment system comprises a radiation source that emits particle radiation, an X-ray emitter located on one side of a target volume and diametrically opposite to the radiation source, and a detector located between the target volume and the radiation source. The target volume is positioned to be exposed to the particle radiation. A radiation direction of the X-ray emitter is oriented opposite to a radiation direction of the particle radiation.

13 Claims, 1 Drawing Sheet

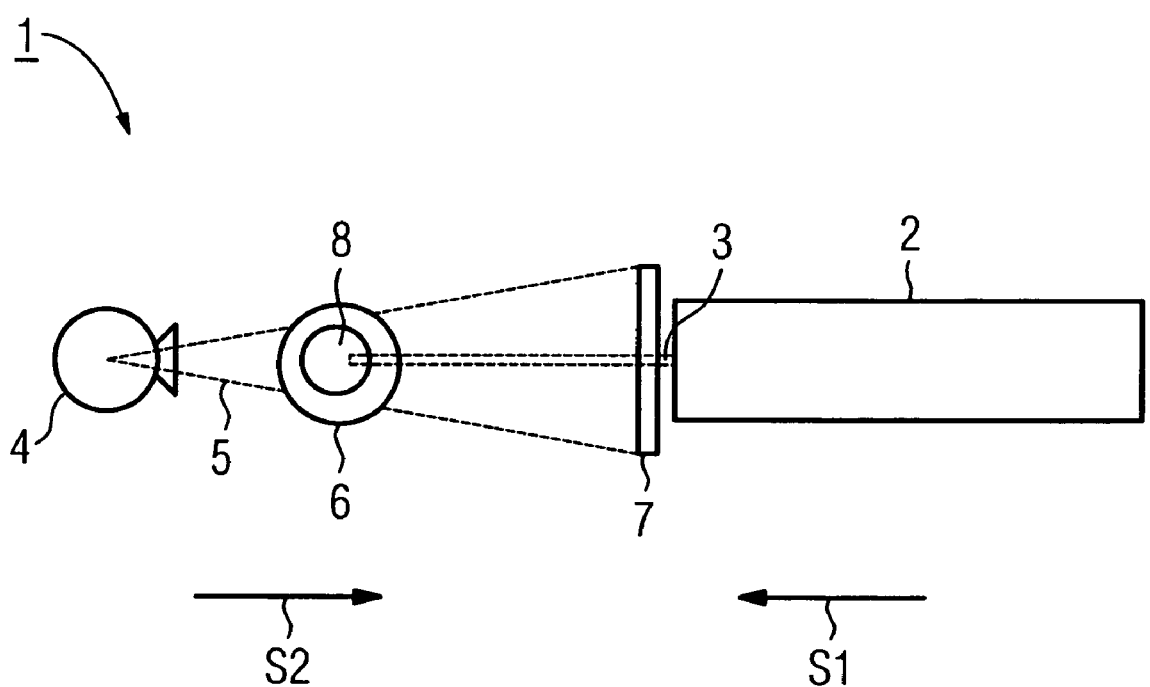

MEDICAL EXAMINATION AND TREATMENT SYSTEM

FIELD

The present embodiments relate, in general, to medical systems, and in particular, to a medical examination and treatment system that uses particle radiation, such as heavy-ion radiation.

BACKGROUND

An irradiation device for heavy-ion therapy is known for example from German Patent Application DE 198 35 209 A1.

In radiation therapy, an exact aiming of a radiation beam at a target tissue to be treated is of great significance and importance. As such, radiation therapy devices are generally combined with diagnostic devices. For example, a medical irradiation system known from German Patent Application DE 35 02 776 A1 includes a simulator with an X-ray tube and an image amplifier for substantially precise positioning of a patient to be examined. In this German Patent Application, a stationary linear accelerator that emits corpuscular rays is for example provided as the radiation source. An additional X-ray emitter, which is provided for diagnostic applications, can be positioned as needed in front of the linear accelerator, or between the linear accelerator and the patient. Before the irradiation begins, the X-ray emitter is removed back out of this position. Alternatively, in the known system, both the linear accelerator and the X-ray emitter may be stationary, but the patient is moved from a diagnosis position to a therapy position. This movement of the patient, however, is a potential source of geometrical inaccuracies in irradiation therapy.

BRIEF SUMMARY

The present embodiments are defined by the appended claims. This summary describes some aspects of the present embodiments and should not be used to limit the claims.

An irradiation device combined with a radiological diagnosis device potentially enables both timesaving irradiation and substantially precise radiation therapy.

A medical examination and treatment system includes a radiation source that emits particle radiation, an X-ray emitter, and a detector. The term radiation source will be understood hereinafter to mean solely a kind of radiation source that emits particles, such as ions or heavy ions. The particle radiation is aimed at a target volume, in which it acts or performs therapeutically, such as for cancer treatment. The X-ray emitter is located on a side of the target volume diametrically opposite the radiation source, and the radiation direction of the X-radiation is oriented counter to that of the particle radiation. The detector is located between the target volume that is to be irradiated with particles and the radiation source.

Throughout an entire examination and treatment, both the radiation source and the X-ray emitter, like the patient, can remain in an unchanged position. As such, geometrical features of the patient, like that of the tissue to be irradiated, that have been diagnosed with the aid of the X-ray device remain unchanged in the ensuing irradiation.

The relatively simple and substantially exact diagnostic capabilities are supplemented by the advantageous properties of the radiation source as a particle radiation source. In contrast to electromagnetic rays, particle beams have an inverted dose profile. The radiation dose deposited in the target volume to be treated increases as the penetration depth increases and has a sharply defined maximum just before a maximum range. A dose profile that is characterized by a Bragg peak is typical for particle radiation. Healthy layers of tissue that are exposed to the radiation are substantially protected. Moreover, particle beams on passing through thick layers of tissue are at most deflected only slightly, and if they are ions, can be focused substantially precisely on the target volume by magnetic lenses. Moreover, with a view to killing off or destroying radiation-resistant tumor cells, ion beams have advantages over electromagnetic beams. Overall, particle therapy is well suited for treating tumors that are poorly accessible or that are close to organs at risk, such as tumors at the base of the skull or in the brain. Particle beams are also suitable for effective treatment of soft-tissue carcinomas and prostate carcinomas, which are surrounded by vulnerable tissue.

The radiation source may emit carbon ions. Alternatively, proton radiation can for example be employed. A radiation source can be employed that emits lithium, oxygen, neon, helium, or other ions. This radiation source involves beams comprising massive particles, and even charged particles. The radiation source may be an accelerator system, such as a system which includes a linear accelerator and a synchrotron ring.

The detector located between the target volume to be treated and the radiation source that emits particles, such as ions, may be supported movably. The detector, which before the particle irradiation is performed serves as an X-radiation detector, can be removed from the beam path of the particle radiation source during the irradiation. Removing the X-radiation detector from its current position in the X-ray examination is generally not contemplated during the particle irradiation, but may potentially occur.

In an alternative feature, the X-radiation detector is located in stationary fashion, and thus remains in the beam path of the radiation source during the particle irradiation as well. The X-radiation detector may be constructed of materials that attenuate or scatter the particle radiation only slightly. In this arrangement, the use of the detector as both an X-radiation detector and a particle radiation detector may be advantageous. During the irradiation, the irradiation profile of the particle beam can thus be monitored with minimal expense for equipment.

An illustrative exemplary embodiment is described in further detail below with reference to, and in conjunction with, a drawing.

BRIEF DESCRIPTION OF THE DRAWING

FIG. 1 shows schematically an embodiment of a medical examination and treatment system.

DETAILED DESCRIPTION

A medical examination and treatment system 1 includes a radiation source 2, which emits particle radiation 3, for example carbon-ion radiation, and which in a manner not shown in further detail is constructed for example to a synchrotron ring combined with a preceding linear accelerator. The system 1 also includes an X-ray emitter 4, which emits an X-ray beam 5. A radiation direction S1 of the particle radiation 3 is oriented counter or opposite to a radiation direction S2 of the X-ray beam 5. The X-ray beam 5 strikes or penetrates a patient 6, and a projection or image is made on a detector 7, which is located between the patient 6 and the radiation source 2. The detector 7 is operable at least as an X-radiation detector, so that before the therapeutic irradiation, the position of the patient 6 can be detected, and if needed, the patient's position relative to the particle beam 3 can be corrected.

The particle radiation 3 is aimed substantially exactly at a target volume 8—shown exaggeratedly large—which indicates the region of the tissue of the patient 6 that is to be treated. In the exemplary embodiment shown, the particle radiation 3 penetrates the detector 7, which simultaneously functions as a particle radiation detector. An additional position monitor is therefore unnecessary. A local distribution of the particle radiation 3, or in other words the beam cross section, can be monitored over the entire duration of the irradiation, via the detector 7. The selected requirements made of the detector are due to its dual use as:

a) an X-radiation detector for imaging, with pixel or volume pixel (voxel) sizes of fractions of a millimeter, and b) a position monitor for the particle beam 3 to, for example, 1/10 of the beam diameter, that is, to approximately 0.1 to 0.2 mm.

For the sake of slight interaction with the particle beam, the detector 7, in the region that serves as a position monitor, may be made of a material with a low (atomic/molecular) weight, may be substantially thin, and may have a substantially homogeneous thickness, so as to affect the beam 5 minimally and uniformly over the beam cross section. Electronics are located, to the extend possible, outside a region that the radiation can pass through, so that for example only a silicon wafer may have radiation passing through it.

Alternatively, in another embodiment, the detector 7 may be movably positioned, for example displaceably or pivotably, in the examination and treatment system 1, to be removed from the beam path 5 of the radiation source 2 during the irradiation. As such, any influence on the particle radiation 3 by the detector 7 is precluded. Any higher absorption of particle beams by the detector 7 in comparison to electromagnetic rays, such as X-rays, is therefore irrelevant. The X-ray emitter 4 is not in operation during the particle irradiation.

The examination and treatment system 1, which in particle therapy operates with inverse beam-eye view imaging, may be suitable for a large, stationary particle radiation source 2, such as a heavy-ion radiation source. Other advantages are offered by the radiation source 2 with a rotatably supported beam delivery, combined with stationary accelerator components, such as a linear accelerator and a synchrotron. A substantially exact aiming of the particle radiation 3 from any direction at the target volume 8, or in other words the diseased organ of the patient 6, is achievable with maximum potential circumvention of adjacent organs at risk.

The invention claimed is:

1. A medical examination and treatment system comprising:
    a radiation source operable to emit particle radiation;
    an X-ray emitter located on one side of a target volume and opposite to the radiation source, the target volume positioned to be exposed to the particle radiation; and
    a detector located between the target volume and the radiation source,
    wherein a radiation direction of the X-ray emitter is oriented opposite to a radiation direction of the particle radiation, and wherein the particle radiation is substantially unchanged by the detector incident from the radiation source to the target volume when the detector is located between the target volume and the radiation source.

2. The medical examination and treatment system of claim 1, wherein the radiation source comprises a proton-emitting radiation source.

3. The medical examination and treatment system of claim 1, wherein the radiation source comprises a carbon ion-emitting radiation source.

4. The medical examination and treatment system of claim 1, wherein the radiation source comprises a lithium ion-emitting radiation source.

5. The medical examination and treatment system of claim 1, wherein the radiation source comprises an oxygen ion-emitting radiation source.

6. The medical examination and treatment system of claim 1, wherein the radiation source comprises a neon ion-emitting radiation source.

7. The medical examination and treatment system of claim 1, wherein the radiation source comprises a helium ion-emitting radiation source.

8. The medical examination and treatment system of claim 1, wherein the detector is supported movably.

9. The medical examination and treatment system of claim 1, wherein the detector is located in stationary fashion in a beam path of the particle radiation.

10. The medical examination and treatment system of claim 1, wherein the detector comprises both an X-radiation detector and a particle radiation detector.

11. The medical examination and treatment system of claim 10, wherein the detector is operable to detect charged particles.

12. The medical examination and treatment system of claim 1, wherein the X-ray emitter and radiation source remain in an unchanged position throughout an examination.

13. The medical examination and treatment system of claim 1, wherein the detector comprises materials that attenuate or scatter the particle radiation only slightly.

* * * * *